(12) United States Patent
Derrien et al.

(10) Patent No.: US 8,981,127 B2
(45) Date of Patent: Mar. 17, 2015

(54) METHOD FOR PREPARING NEBIVOLOL

(75) Inventors: Yvon Derrien, La Meignanne (FR); Eric Chenard, Angers (FR); Alain Burgos, Les Ponts de Ce (FR)

(73) Assignee: Zach System, Avrille (FR)

( * ) Notice: Subject to any disclaimer, the term of this patent is extended or adjusted under 35 U.S.C. 154(b) by 1028 days.

(21) Appl. No.: 13/120,690

(22) PCT Filed: Sep. 22, 2009

(86) PCT No.: PCT/FR2009/051775
§ 371 (c)(1),
(2), (4) Date: May 31, 2011

(87) PCT Pub. No.: WO2010/034927
PCT Pub. Date: Apr. 1, 2010

(65) Prior Publication Data
US 2011/0237808 A1  Sep. 29, 2011

(30) Foreign Application Priority Data
Sep. 24, 2008 (FR) ...................... 08 56415

(51) Int. Cl.
*C07D 311/00* (2006.01)
*C07D 301/27* (2006.01)
*C07D 301/02* (2006.01)
*C07D 311/58* (2006.01)
*C07D 311/66* (2006.01)
*C07D 407/04* (2006.01)

(52) U.S. Cl.
CPC ............ *C07D 311/58* (2013.01); *C07D 311/66* (2013.01); *C07D 407/04* (2013.01)
USPC ............ 549/405; 549/519; 549/516; 549/515

(58) Field of Classification Search
CPC ... C07D 311/58; C07D 301/24; C07D 301/30
USPC .................................. 549/405, 519, 151, 516
See application file for complete search history.

(56) References Cited

U.S. PATENT DOCUMENTS

| 5,591,885 | A | | 1/1997 | Hilpert | |
|---|---|---|---|---|---|
| 6,127,556 | A | * | 10/2000 | Liu et al. ...................... | 549/519 |
| 7,560,575 | B2 | * | 7/2009 | Bader et al. ................... | 549/407 |
| 7,960,572 | B2 | * | 6/2011 | Volpicelli et al. ............. | 549/398 |
| 8,623,873 | B2 | * | 1/2014 | Gilbert et al. ............. | 514/253.01 |

FOREIGN PATENT DOCUMENTS

WO   WO 2008/040528   4/2008

* cited by examiner

*Primary Examiner* — Andrew D Kosar
*Assistant Examiner* — Raymond Covington
(74) *Attorney, Agent, or Firm* — Silvia Salvadori, P.C.

(57) ABSTRACT

The present invention relates to a process for the preparation of nebivolol and, more particularly, to an improved process of synthesizing an alpha-haloketone of formula

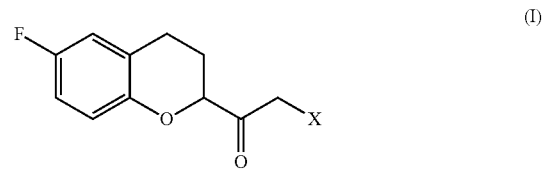

(I)

a key intermediate in the preparation of nebivolol.

17 Claims, No Drawings

METHOD FOR PREPARING NEBIVOLOL

This application is a U.S. national stage of PCT/FR2009/051775 filed on Sep. 22, 2009 which claims priority to and the benefit of French Application No. 0856415 filed on Sep. 24, 2008, the contents of which are incorporated herein by reference.

The present invention relates to a process for the preparation of nebivolol and, more particularly, to an improved method of synthesizing an alpha-haloketone of formula

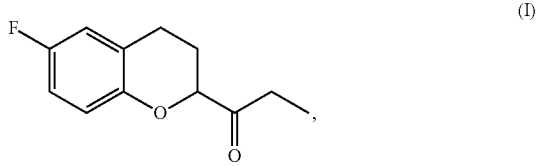

(I)

a key intermediate in preparing nebivolol.

BACKGROUND OF THE INVENTION

Nebivolol (hereafter NBV), is a mixture of equal amounts of [2S [2R*[R[R*]]]]α,α'-[imino-bis(methylene)]bis[6-fluoro-chroman-2-methanol] (hereafter d-NBV) of formula (IA)

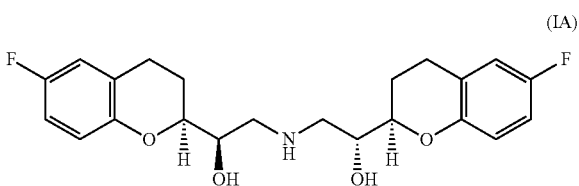 [SMILES: O[C@H](CNC[C@@H](O)[C@H]1CCc2cc(F)ccc2O1)[C@@H]1CCc2cc(F)ccc2O1]

(IA)

and its [2R [2S*[S[S*]]]] enantiomer (hereafter l-NBV) of formula (IB)

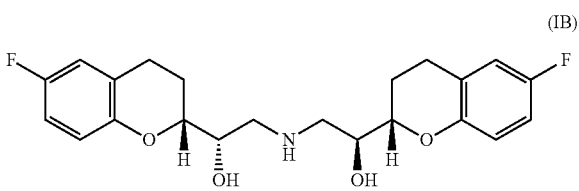 [SMILES: O[C@@H](CNC[C@H](O)[C@H]1CCc2cc(F)ccc2O1)[C@@H]1CCc2cc(F)ccc2O1]

(IB)

Nebivolol is characterised by its β-adrenergic blocking properties and is useful in treating essential hypertension. It has basic properties and may be converted into its addition salts through treatment with suitable acids. The hydrochloric acid addition salt is the marketed product.

It is known in the art that the synthesis of α,α'-[imino-bis(methylene)]bis[chroman-2-methanol] molecular structures is challenging for the skilled person because of the 4 asymmetric carbon atoms producing a mixture of 16 stereoisomers (in case of asymmetrical substitutions) or a mixture of 10 stereoisomers (in case of symmetrical substitutions). As apparent from the presence of symmetry in the structure of nebivolol, a total of 10 stereoisomers may be generated.

Literature reports several processes for the preparation of nebivolol.

Patent EP 145067 describes a process of preparing NBV which comprises synthesizing diastereoisomeric mixtures of chroman epoxide derivatives in accordance with the synthetic scheme below

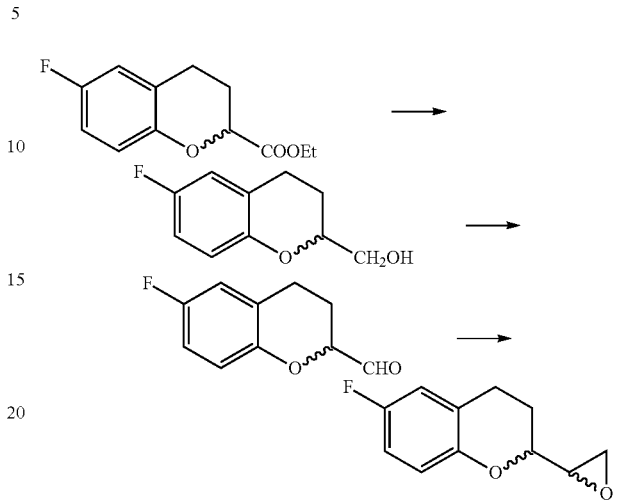

The 6-fluoro chroman carboxylic acid ethyl ester, derived from the esterification of the corresponding acid, is reduced with sodium dihydro bis-(2-methoxyethoxy)-aluminate to a primary alcohol; the product is reacted with oxalyl chloride and then triethylamine at −60° C. to give the corresponding racemic aldehyde, which is then converted into an epoxide as a mixture of (R,S), (S,R), (R,R) and (S,S) stereoisomers.

Said epoxide derivatives represent the key intermediates of the process.

Patent EP 334429 mainly describes the same synthetic process reported in the previous patent and is particularly directed to the preparation of the single optical isomers (R,S, S,S) and (S,R,R,R) of NBV.

In this instance, the 6-fluoro chroman carboxylic acid is resolved into single enantiomers by treatment with (+)-dehydroabiethylamine. Said single enantiomers are separately converted into their corresponding epoxides resulting in a mixture of two diastereoisomers. The following synthetic scheme describes, for example, the conversion of the S-acid derivative.

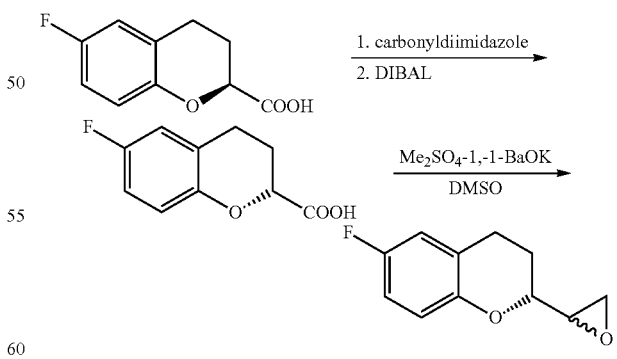

Co-pending international patent application WO 2008/040528 in the name of the same Applicant describes an improved process for the preparation of 6-fluorochroman epoxides via alpha-haloketone which comprises the conversion of an alkyl or aryl 6-fluoro-3,4-dihydro-2H-chromen-2-carboxylate into 2-halo-1-(6-fluoro-3,4-dihydro-2H- chromen-2-yl)-ethanone; reducing said alpha-haloketone derivative to give the corresponding 2-halo-1-(6-fluoro-3,4-dihydro-2H-chromen-2-yl)-ethanol; and cyclizing in the presence of a base to give an epoxide derivative as a mixture of four stereoisomers.

In particular, said conversion step is carried out by reacting an alkyl or aryl chroman carboxylate with a sulfoxonium ylide to give the keto sulfoxonium ylide which is transformed into an alpha-haloketone by reaction with anhydrous halogenhydric acids optionally generated in situ.

International patent application WO 2008/010022 (Cimex Pharma and University of Zurich) describes a process of making racemic nebivolol and its pure enantiomers and pharmaceutically acceptable salts thereof.

The method entails, inter alia, providing a racemic alpha-haloketone of formula

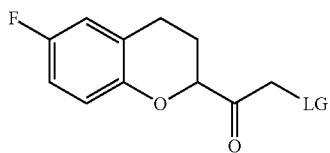

(V)

and its conversion into a 6-fluoro-chroman epoxide; in particular said step of providing a compound of formula V comprises (1) transforming a compound of formula

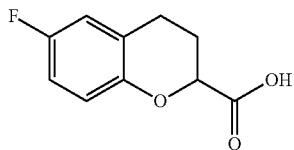

(II)

into an activated acid derivative;

(2) reacting the activated acid derivative with Meldrum's acid in the presence of a base to give a compound of formula

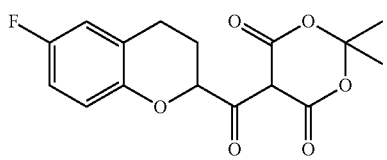

(III)

(3) converting the compound of formula III into a compound of formula

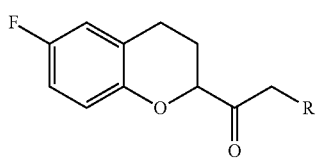

(IV)

wherein R is hydrogen or COOR' and wherein R' is $C_1$-$C_6$ alkyl or aryl-$C_1$ alkyl; and (4) halogenating the compound of formula IV and optionally conducting hydrolysis and decarboxylation to give the compound of formula V.

It is apparent from the prior art that alpha-haloketones play an essential role in the preparation of 6-fluoro-chroman epoxide derivatives and, in turn, of the active pharmaceutical ingredient nebivolol.

Purpose of the Invention

Hence, it would be desirable to study alternative methods for preparing the intermediate of formula I in racemic form or in the form of its single stereoisomers with good yields and under conditions more favourable from the industrial application point of view.

SUMMARY OF THE INVENTION

We have now surprisingly found an easy and efficient alternative synthesis of 2-halo-1-(6-fluoro-3,4-dihydro-2H-chromen-2-yl)-ethanone derivatives, key intermediates in preparing nebivolol, which allows to overcome the drawbacks of the processes described in the prior art.

DETAILED DESCRIPTION OF THE INVENTION

Therefore, a first object of the present invention is a process for preparing a compound of formula

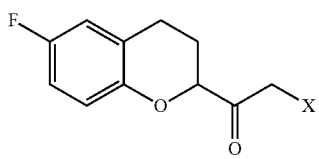

(I)

wherein X is a halogen atom, which comprises reacting a compound of formula

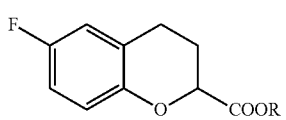

(VI)

wherein R is a ($C_1$-$C_6$)-alkyl group; with a halomethyllithium derivative.

The compounds of formula VI are known intermediates in the preparation of NBV, whose preparation is extensively described in the art, see, for example, the above cited patents EP 145067 and EP 334429.

The halomethyllithium according to the invention can be represented by the formula Li—$CH_2$—X.

wherein X is defined above; and can be prepared by reaction of an organolithium compound and a di-halomethane.

In a preferred embodiment of the invention, said organolithium compound and said di-halomethane are added to a reaction solvent and the halomethyllithium reactant is formed in the reaction system.

Preferred halomethyllithium compounds are chloromethyllithium and bromomethyllithium, the former being more preferred.

Preferred organolithium compounds are methyllithium, n-butyllithium and sec-butyllithium, n-butyllithium being more preferred.

Preferred di-halomethanes used in the invention are bromochloromethane, dibromomethane and chloroiodomethane, the former being the most preferred one. Since it is known in the art that halomethyllithium derivatives are thermally unstable, it is preferable that an ester compound of formula VI and a dihalomethane are dissolved beforehand in a solvent and the organolithium compound is then added.

The preferred solvent of the invention is an ether-type solvent, such as tetrahydrofuran, diethyl ether, tert-butylmethyl ether and the like. Mixtures of an ether type solvent and a non-polar solvent, such as toluene, hexane and the like, can be used in the reaction object of the invention.

Generally, the addition of the halomethyllithium reagent to the compound of formula VI is carried out at a temperature comprised between −100° C. and 0° C. The reaction is preferably carried out in the range of −85° C. to −50° C.

When the reaction is complete it is generally preferable to treat the obtained reaction mixture with an ammonium chloride aqueous solution, a phosphate buffer solution, water or an acid, preferably a weak acid such as acetic acid and the like.

The amount of organolithium compound and dihalomethane used in the invention is not particularly critical. Preferably, the ester substrate, the dihalomethane reactant and the organolithium compound are used in a molar ratio of about 1:2:2.

In the present invention the term halogen means a fluorine, chlorine, bromine or iodine atom.

X is preferably a chlorine or bromine atom, a chlorine atom being more preferred.

A further object of the present invention is a process for preparing a compound of formula

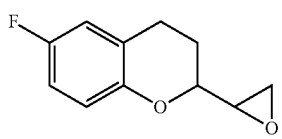
(VII)

which comprises a conversion of a compound of formula VII into a compound of formula I in accordance with what is reported above.

A further object of the present invention is a process for preparing a compound of formula

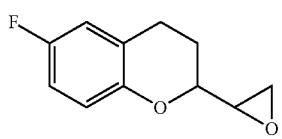
(VII)

according to what is reported above, further comprising
a) the reduction of a compound of formula I to give a compound of formula

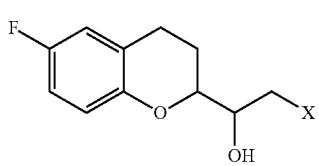
(VIII)

b) the reaction of said compound of formula VIII with a base to give the epoxide compound of formula VII.

The reduction of a compound of formula I to give a compound of formula VIII (step a) is carried out according to known techniques.

In one embodiment of the invention said reduction is carried out in accordance with co-pending international patent application WO 2008/040528.

Preferably, the reaction is carried out by reacting a compound of formula I with sodium borohydride in the presence of an alcoholic solvent, optionally mixed with water. The preferred solvent is ethanol.

The reaction of a compound of formula VIII to give a compound of formula VII (step b) is carried out in the presence of a base in accordance with known techniques. Again, in one embodiment of the invention said cyclization reaction is carried out in accordance with co-pending international patent application WO 2008/040528. Cyclization is preferably carried out by reacting a compound of formula VIII with alkaline alkoxides or hydroxides in the presence of alcoholic solvents or ethers optionally in admixture.

A preferred embodiment of the invention is that the reaction is carried out with a base such as potassium t-butoxide in the presence of an isopropanol/THF mixture. Alternatively, the reaction is carried out with a base such as sodium hydroxide in the presence of isopropanol.

In an another embodiment of the invention, a compound of formula VII is prepared by a one-pot procedure starting from an ester derivative of formula VI.

Said procedure entails reacting the ester substrate with a halomethyllithium derivative and an in situ reduction/cyclization to directly provide epoxide compounds of formula VII.

The reaction mixture resulting from the addition of the halomethyllithium derivative to the compound of formula VI is in practice reduced in situ to give a halohydrin of formula VIII which is in turn cyclised in the presence of a base.

Therefore, a further object of the present invention is a process for preparing a compound of formula

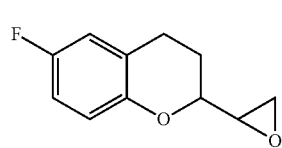
(VII)

which comprises reacting a compound of formula

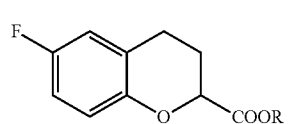
(VI)

wherein R is defined above; with a halomethyllithium derivative to give a reaction mixture; the in situ reduction of said reaction mixture; and cyclization in the presence of a base.

In a preferred embodiment of the invention said reaction mixture is reduced in situ with a borane reagent; the resulting lithium alkoxyborohydride rearranges in situ and is hydrolyzed to a halohydrin which is, in turn, cyclised in the presence of alkali alkoxides or hydroxides.

Preferably, the in situ reduction according to the invention is carried out with $BH_3$ in THF.

It has been observed by the inventors that the reaction mixture coming from the addition of the halomethyllithium derivative to the compound of formula VI comprises as major chemical entity a compound of formula

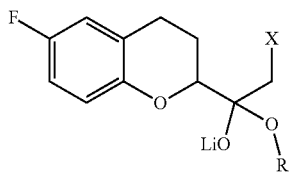

(IX)

wherein X and R are defined above; which undergoes the in situ reduction according to the invention.

Said compound of formula IX is a further object of the invention.

It is thus evident that the process object of the invention constitutes an alternative synthesis for the preparation of chroman epoxides which is efficient, economic and suitable for industrial production; in addition, the availability of the raw materials used, together with the reduced number of synthetic steps and the nearly quantitative yields obtained, give notable benefits in terms of process costs and efficiency. Furthermore, the efficiency of the chemical reactions in only one reactor (one-pot reaction) is much desired by chemists because a lengthy separation process and purification of the intermediate chemical compounds is avoided, which does save time and resources while increasing the chemical yield.

In addition, the method of converting an ester into an alpha-haloketone and the one-pot conversion of the ester into an epoxide according to the invention are stereoconservative for substrates endowed with chiral centres.

The process of the invention may thus be applied to optically active esters of formula VI which can be obtained by esterifying the corresponding optically active acid or, alternatively, by chiral chromatography in accordance with known techniques. Therefore, it is evident to the skilled person that the process object of the invention leads to the preparation of enantiomerically enriched alpha-haloketone of formula I and to epoxide derivatives in racemic form comprising a mixture of two diastereoisomers, see schemes below:

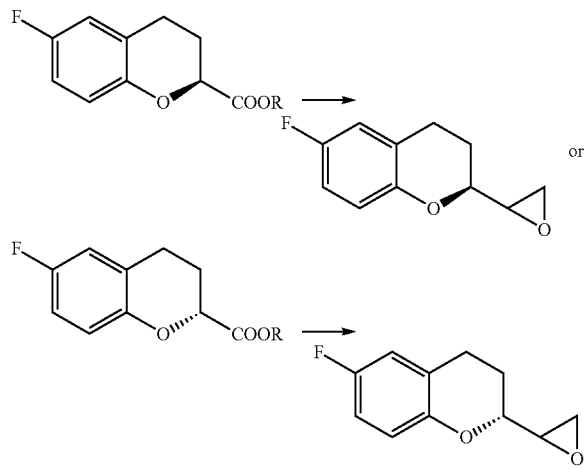

As known, said partially resolved epoxide derivatives represent key intermediates in the preparation of NBV.

A further object of the present invention is a process for synthesizing nebivolol, characterised by the fact that the preparation of a compound of formula

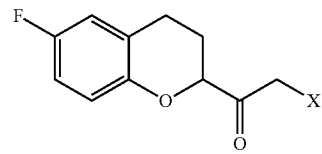

(I)

wherein X is a halogen atom; comprises reacting a compound of formula

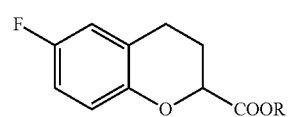

(VI)

wherein R is a $(C_1-C_6)$-alkyl group; with a halomethyllithium derivative.

A further object of the present invention is a process for synthesizing nebivolol which comprises a one-pot conversion of a compound of formula VI into a compound of formula VII in accordance with what is reported above.

A practical embodiment of the process object of the present invention comprises the conversion of a 6-fluoro chroman carboxylate of formula VI into an alpha-haloketone of formula I by addition of a halomethyllithium derivative; said alpha-haloketone of formula I is reduced to a halohydrin of formula VIII and cyclised to an epoxide derivative of formula VII in the presence of a base.

A preferred practical embodiment of the process object of the present invention comprises the conversion of a $(C_1-C_6)$-alkyl 6-fluoro chroman carboxylate of formula VI into the corresponding alpha-chloroketone of formula I by addition of a chloromethyllithium derivative, preferably generated in situ by reacting bromochloromethane or iodochloromethane with an organolithium derivative such as n-butyllithium; said alpha-chloroketone of formula I is reduced to a chlorohydrin of formula VIII by means of a reaction with sodium borohydride in the presence of an alcoholic solvent and cyclised to an epoxide derivative of formula VII by reaction with alkali alkoxides or hydroxides in the presence of alcoholic solvents or ethers optionally in admixture.

Another practical embodiment of the process object of the present invention comprises the one-pot conversion of a 6-fluoro chroman carboxylate of formula VI into an epoxide derivative of formula VII by addition of a halomethyllithium derivative; in situ reduction of the thus obtained reaction mixture; and cyclization in the presence of a base.

Another preferred practical embodiment of the process object of the present invention comprises the conversion of a $(C_1-C_6)$-alkyl 6-fluoro chroman carboxylate of formula VI into an epoxide derivative of formula VII by addition of a chloromethyllithium derivative, preferably generated in situ by reacting bromochloromethane or iodochloromethane with an organolithium derivative such as n-butyllithium, to give a reaction mixture; said mixture is reduced in situ with $BH_3$ in the presence of THF and cyclised to an epoxide derivative of formula VII by reacting with alkali alkoxides or hydroxides.

The invention will be now better illustrated by the following examples.

In all the examples, and unless otherwise stated, the percentages are expressed by weight, the temperature is expressed in degrees Celsius and the pressure is atmospheric pressure.

Example 1

Synthesis of 6-fluoro-4-oxo-4H-1-benzopyran-2-carboxylic acid

A solution of 20 g of 5'-fluoro-2'-hydroxyacetophenone (13 mol) in 100 ml of THF was slowly added at 5-10° C. to a solution of 52 ml of 30% sodium methoxide in methanol (0.30 mol). The temperature was then allowed to reach 15° C. and 22 g of diethyloxalate (0.15 mol) were added between 15 to 25° C. to give a complete solution. The reaction progress was monitored by TLC until less than 5% of raw starting material was present. The mixture was adjusted to pH 1-2 by the addition of 20 ml of 36% HCl (0.24 mol) and 100 ml of water between 5 to 15° C. The solid residue formed was removed by filtration then the aqueous layer removed by decantation. The organic layer was then washed with 40 ml of an aqueous solution of 15% NaCl and concentrated under reduced pressure at 40-50° C. to give a yellow oil. This residual oil was dissolved in 100 ml of glacial acetic acid and 100 ml of water at reflux for 17-20 h. After cooling to 15-20° C., the suspension of the title compound was filtered to give after drying 20 g of a white or off-white solid (yield: 75%). A second crop can be obtained after concentration of the mother liquor and the residue warmed up in 50 ml glacial acetic acid and 50 ml water to reflux for 20 h to hydrolyze the ester to give an additional batch of the title compound (2-3 g).

Example 2

Synthesis of 6-fluoro-1-benzopyran-2-carboxylic acid methyl ester 20 g of 6-fluoro-4-oxo-4H-1-benzopyran-2-carboxylic acid (96 mmol) were hydrogenated under 4 bars of hydrogen in 200 ml THF with 2 g of methanesulfonic acid (20 mmol) and 2 g of 5% Pd on charcoal (Type Escat 112, Engelhard) at 45-55° C. until consumption of hydrogen was no longer observed. The reaction progress was monitored by TLC. The catalyst was then removed by filtration and the reaction mixture concentrated to 40 ml under reduced pressure. 100 ml of methanol were then added and the mixture (solution) was stirred at 20-25° C. until less than 1% of 6-fluoro-3,4-dihydro-2H-chromen-2-carboxylic acid was detected (TLC). The solution was then concentrated under reduced pressure and the residue was dissolved in 60 ml of THF then concentrated under reduced pressure to remove water by azeotropic distillation to give 20 g of the title compound (yield: 100%).

$\delta_H$ (400 MHz; CDCl$_3$) 6.89-6.79 (2H, m, Ar), 6.77-6.76-6.72 (1H, m, Ar), 4.73-4.69 (1H, m), 3.79 (3H, s), 2.87-2.69 (2H, m), 2.31-2.12 (2H, m).

Example 3

Synthesis of 2-chloro-1-(6-fluoro-1-benzopyran-2-yl)-ethanone 1.2 g of bromochloromethane (9.2 mmol) were added at room temperature to a solution of 1.0 g of crude 6-Fluoro-1-benzopyran-2-carboxylic acid methyl ester (4.7 mmol) in 15 ml of THF. The solution was then cooled to −80/−85° C. and 4.6 ml of 2.5 M n-BuLi in hexane (9.2 mmol) were slowly added to maintain the internal temperature between −75° C. and −80° C. The reaction progress was monitored by TLC. The solution was then acidified by the addition of 1 ml glacial acetic acid in 2 ml THF between −70° C. and −80° C. 5 ml of water were then added at 0° C. and the aqueous layer was then removed after decantation. The organic layer was concentrated under reduced pressure to give the title compound (1.05 g) as a yellow oil (titration by NMR: ≈80% w/w).

$\delta_H$ (400 MHz; CDCl$_3$) 6.86-6.83 (2H, m, Ar), 6.80-6.75 (1H, m, Ar), 4.69-4.65 (1H, m), 4.63 (1H, d, J 16.8), 4.47 (1H, d, J 16.8), 2.91-2.72 (2H, m), 2.34-2.26 (1H, m), 2.13-2.03 (1H, m); m/z (EI) 228.035339 (M$^+$ C$_{11}$H$_{10}$ClFO$_2$ requires 228.03551).

Example 4

Synthesis of 2-chloro-1-(6-fluoro-1-benzopyran-2-yl)-ethanol

A stirred solution of 2-Chloro-1-(6-fluoro-1-benzopyran-2-yl)-ethanone (0.33 g, 1.28 mmol, 88.4% A) in ethanol (2.5 ml) was cooled to 0° C. under nitrogen. NaBH$_4$ (60.1 mg, 1.59 mmol) was added to the solution and the reaction mixture stirred for 2 hours. After checking by GPC that the starting product had disappeared, the mixture was diluted with demineralized water (7 ml) and dichloromethane (7 ml) and the phases separated. The organic layer was dried over anhydrous sodium sulphate, filtered and concentrated under vacuum to give crude 2-Chloro-1-(6-fluoro-1-benzopyran-2-yl)-ethanol as a mixture of diastereoisomers 54:46 (0.30 g, 70% yield, 67.9% A).

$\delta_H$ (400 MHz; CDCl$_3$) 6.83-6.70 (6H, m, Ar), 4.21-4.16 (1H, m), 4.02-3.96 (1H, m), 3.94-3.88 (3H, m), 3.86-3.77 (2H, m), 3.74-3.68 (1H, m), 2.97-2.74 (4H, m), 2.30-2.21 (2H, m), 2.29-2.22 (1H, m), 2.02-1.96 (2H, m), 1.89-1.78 (1H, m); m/z (EI) 230.050989 (M$^+$ C$_{11}$H$_{12}$ClFO$_2$ requires 230.05067).

Example 5

Synthesis of 6-fluoro-2-oxiranyl-1-benzopyran

2-Chloro-1-(6-fluoro-1-benzopyran-2-yl)-ethanol (2.5 g, 9.20 mmol, 84.9% A) was dissolved in i-PrOH (25 ml) under nitrogen and the reaction mixture cooled to 0° C. A 2M aqueous solution of NaOH (12.5 ml) was added to the solution over 5 min and the reaction was stirred for 1 hour 30 min. The reaction mixture was then diluted with toluene (50 ml) and the pH corrected with acetic acid (0.92 g). Toluene (50 ml) and demineralized water (10 ml) were then added to the mixture and the phases separated after extraction. The collected organic phases were then washed with demineralized water (50 ml). The toluene phase was then anhydrified by azeotropic distillation and concentrated until dryness in a rotary evaporator to give 6-Fluoro-2-oxiranyl-1-benzopyran as a mixture of diastereoisomers 52:48 (2.0 g, 96% yield, 86.1% A).

Diast. RR,SS: $\delta_H$ (400 MHz; CDCl$_3$) 6.81-6.72 (3H, m), 3.88-3.82 (1H, m), 3.21-3.17 (1H, m), 2.89-2.76 (4H, m), 2.1-2.00 (1H, m), 1.97-1.87 (1H, m); Diast. SR,SR: $\delta_H$ (400 MHz; CDCl$_3$) 6.84-6.73 (3H, m), 3.87-3.81 (1H, m), 3.15-3.10 (1H, m), 2.91-2.78 (4H, m), 2.18-2.10 (1H, m), 1.96-1.84 (1H, m).

Example 6

Synthesis of 2-chloro-1-((R)-6-fluoro-1-benzopyran-2-yl)-ethanone 2.5 g of bromochloromethane (18.8 mmol) were added at room temperature to a solution of 2.0 g of (R)-6-Fluoro-1- benzopyran-2-carboxylic acid methyl ester, obtained after separation of the corresponding racemic mixture on a chiral chromatography column (9.4 mmol, 96.6% A, ee>99%), in 40 ml THF. The solution was then cooled to −80/−85° C. and 7.7 ml of 2.5 M n-BuLi in hexane (19 mmol) were slowly added to maintain the internal temperature between −75° C. and −80° C. The reaction progress was monitored by TLC. The solution was then acidified by the addition of 2 ml glacial acetic acid in 2 ml THF between −70° C. and −80° C. 10 ml of water were then added at −20/0° C. and the aqueous layer was then removed after decantation. The organic layer was concentrated under reduced pressure to give the title compound (2.2 g) as a white-off solid (ee: 97.2%, 94.8% A).

Optionally, the solid was then recrystallized from a mixture of ethyl acetate and hexane to give 1.73 g of 2-Chloro-1-((R)-6-fluoro-1-benzopyran-2-yl)-ethanone as a white-off solid (80% yield, ee: 99%, 97.6% A, $[α]_D$: −27°).

CHIRAL OB—H 250*4.6 mm particles 5 N-Heptane-IPOH (95V-5V), 200 nm, (R) enantiomer RT=20.6 min, (S) enantiomer 22.2 min.

$δ_H$ (400 MHz; CDCl$_3$) 6.86-6.83 (2H, m, Ar), 6.80-6.75 (1H, m, Ar), 4.69-4.65 (1H, m), 4.63 (1H, d, J 16.8), 4.47 (1H, d, J 16.8), 2.91-2.72 (2H, m), 2.34-2.26 (1H, m), 2.13-2.03 (1H, m).

Example 7

Synthesis of 2-chloro-1-((S)-6-fluoro-1-benzopyran-2-yl)-ethanone 2.5 g of bromochloromethane (18.8 mmol) were added at room temperature to a solution of 2.0 g of crude (S)-6-Fluoro-1-benzopyran-2-carboxylic acid methyl ester, obtained after separation of the corresponding racemic mixture on a chiral chromatography column (9.4 mmol, 87.9% A, ee>99%), in 40 ml THF. The solution was then cooled to −80/−85° C. and 7.7 ml of 2.5 M n-BuLi in hexane (19 mmol) were slowly added to maintain the internal temperature between −75° C. and −80° C. The reaction progress was monitored by TLC. The solution was then acidified by the addition of 2 ml glacial acetic acid in 2 ml THF between −70° C. and −80° C. 10 ml of water were then added at −20/0° C. and the aqueous layer was then removed after decantation. The organic layer was concentrated under reduced pressure to give the title compound (2.54 g) as a yellow oil (ee: 99%, 94.8% A).

Optionally, the oil was then purified by chromatography to give 1.66 g of 2-Chloro-1-((S)-6-fluoro-1-benzopyran-2-yl)-ethanone as a white-off solid (76% yield, ee: 99%, 96.1% A, $[α]_D$: +21°).

CHIRAL OB—H 250*4.6 mm particles 5 N-Heptane-IPOH (95V-5V), 200 nm, (R) enantiomer RT=20.6 min, (S) enantiomer 22.2 min.

$δ_H$ (400 MHz; CDCl$_3$) 6.86-6.83 (2H, m, Ar), 6.80-6.75 (1H, m, Ar), 4.69-4.65 (1H, m), 4.63 (1H, d, J 16.8), 4.47 (1H, d, J 16.8), 2.91-2.72 (2H, m), 2.34-2.26 (1H, m), 2.13-2.03 (1H, m)

Example 8

Synthesis of a mixture of (S)-2-chloro-1-((R)-6-fluoro-1-benzopyran-2-yl)-ethanol and (R)-2-chloro-1-((R)-6-fluoro-1-benzopyran-2-yl)-ethanol A stirred solution of 2-Chloro-1-((R)-6-fluoro-1-benzopyran-2-yl)-ethanone (0.7 g, 3.06 mmol, 97.6% A) in ethanol (10 ml) was cooled to 0° C. under nitrogen. NaBH$_4$ (152 mg, 4 mmol) was added to the solution and the reaction mixture stirred for 2 hours. After checking by GPC that the starting product had disappeared, the mixture was diluted with water (17 ml) and dichloromethane (17 ml) and the phases separated. The organic layer was dried over anhydrous sodium sulphate, filtered and concentrated under vacuum to give a mixture of diastereoisomers of (S)-2-chloro-1-((R)-6-fluoro-1-benzopyran-2-yl)-ethanol and (R)-2-Chloro-1-((R)-6-fluoro-1-benzopyran-2-yl)-ethanol 55:45 (0.7 g, 100% yield, 97.1% A).

CHIRALPACK AD-H (250×4.6) mm particles 5 μm, N-Heptane-IPOH (95V-5V), 281 nm, (S)-2-Chloro-1-((R)-6-fluoro-1-benzopyran-2-yl)-ethanol: RT=35.7 min; (R)-2-Chloro-1-((R)-6-fluoro-1-benzopyran-2-yl)-ethanol: RT=50.4 min.

$δ_H$ (400 MHz; CDCl$_3$) 6.83-6.70 (6H, m, Ar), 4.21-4.16 (1H, m), 4.02-3.96 (1H, m), 3.94-3.88 (3H, m), 3.86-3.77 (2H, m), 3.74-3.68 (1H, m), 2.97-2.74 (4H, m), 2.30-2.21 (2H, b, —OH), 2.29-2.22 (1H, m), 2.02-1.96 (2H, m), 1.89-1.78 (1H, m); m/z (EI) 230.050989 (M$^+$ C$_{11}$H$_{12}$ClFO$_2$ requires 230.05067).

Example 9

Synthesis of a mixture of (R)-2-chloro-1-((S)-6-fluoro-1-benzopyran-2-yl)-ethanol and (S)-2-chloro-1-((S)-6-fluoro-1-benzopyran-2-yl)-ethanol A stirred solution of 2-Chloro-1-((S)-6-fluoro-1-benzopyran-2-yl)-ethanone (0.7 g, 3.06 mmol, 96.1% A) in ethanol (10 ml) was cooled to 0° C. under nitrogen. NaBH$_4$ (152 mg, 4 mmol) was added to the solution and the reaction mixture stirred for 2 hours. After checking by GPC that the starting product had disappeared, the mixture was diluted with water (17 ml) and dichloromethane (17 ml) and the phases separated. The organic layer was dried over anhydrous sodium sulphate, filtered and concentrated under vacuum to give a mixture of diastereoisomers of (R)-2-Chloro-1-((S)-6-fluoro-1-benzopyran-2-yl)-ethanol and (S)-2-Chloro-1-((S)-6-fluoro-1-benzopyran-2-yl)-ethanol 55:45 (0.706 g, 100% yield, 97.1% A).

CHIRALPACK AD-H (250×4.6) mm particles 5 μm, N-Heptane-IPOH (95V-5V), 281 nm, (R)-2-Chloro-1-((S)-6-fluoro-1-benzopyran-2-yl)-ethanol: RT=39.8 min; (S)-2-Chloro-1-((S)-6-fluoro-1-benzopyran-2-yl)-ethanol: RT=58.4 min.

$δ_H$ (400 MHz; CDCl$_3$) 6.83-6.70 (6H, m, Ar), 4.21-4.16 (1H, m), 4.02-3.96 (1H, m), 3.94-3.88 (3H, m), 3.86-3.77 (2H, m), 3.74-3.68 (1H, m), 2.97-2.74 (4H, m), 2.30-2.21 (2H, b, —OH), 2.29-2.22 (1H, m), 2.02-1.96 (2H, m), 1.89-1.78 (1H, m); m/z (EI) 230.050989 (M$^+$ C$_{11}$H$_{12}$ClFO$_2$ requires 230.05067).

Example 10

Synthesis of a mixture of (R)-6-fluoro-2-(S)-oxiranyl-1-benzopyran and (R)-6-fluoro-2-(R)-oxiranyl-1-benzopyran A mixture of (S)-2-Chloro-1-((R)-6-fluoro-1-benzopyran-2-yl)-ethanol and (R)-2-Chloro-1-((R)-6-fluoro-1-benzopyran-2-yl)-ethanol 55:45 (0.7 g, 3.03 mmol, 97.1% A) was dissolved in i-PrOH (8 ml) under nitrogen and the reaction mixture cooled to 0-5° C. A 2M aqueous solution of NaOH (4.1 ml) was added to the solution over 5 min and the reaction mixture was stirred for 1 hour 30 min at 0-5° C. then stirred overnight at room temperature. The reaction mixture was then diluted with toluene (14 ml) and the pH corrected with acetic acid (0.305 g). Toluene (14 ml) and water (1.5 ml) were then added to the mixture and the phases separated after extraction. The collected organic phases were then washed with water (14 ml). The toluene phase was then anhydrified by azeotropic distillation and concentrated until dryness in a rotary evaporator to give a mixture of diastereoisomers of (R)-6-Fluoro-2-(S)-oxiranyl-1-benzopyran and (R)-6-Fluoro-2-(R)-oxiranyl-1-benzopyran 52:48 (0.56 g, 95% yield, 94.4% A).

CHIRALPACK AD-H (250×4.6) mm particles 5 μm, N-Heptane-IPOH (95V-5V), 281 nm, (R)-6-Fluoro-2-(S)-oxiranyl-1-benzopyran: RT=14.4 min; (R)-6-Fluoro-2-(R)-oxiranyl-1-benzopyran: RT=18.2 min.

Diast. RR: $\delta_H$ (400 MHz; CDCl$_3$) 6.81-6.72 (3H, m), 3.88-3.82 (1H, m), 3.21-3.17 (1H, m), 2.89-2.76 (4H, m), 2.1-2.00 (1H, m), 1.97-1.87 (1H, m); Diast. RS: $\delta_H$ (400 MHz; CDCl$_3$) 6.84-6.73 (3H, m), 3.87-3.81 (1H, m), 3.15-3.10 (1H, m), 2.91-2.78 (4H, m), 2.18-2.10 (1H, m), 1.96-1.84 (1H, m).

Example 11

Synthesis of a mixture of (S)-6-fluoro-2-(R)-oxiranyl-1-benzopyran and (S)-6-fluoro-2-(S)-oxiranyl-1-benzopyran A mixture of diastereoisomers of (R)-2-Chloro-1-((S)-6-fluoro-1-benzopyran-2-yl)-ethanol and (S)-2-Chloro-1-((S)-6-fluoro-1-benzopyran-2-yl)-ethanol 55:45 (0.7 g, 3.03 mmol, 97.1% A) was dissolved in i-PrOH (8 ml) under nitrogen and the reaction mixture cooled to 0-5° C. A 2 M aqueous solution of NaOH (4.1 ml) was added to the solution over 5 min and the reaction was stirred for 1 hour 30 min at 0-5° C. then stirred overnight at room temperature. The reaction mixture was then diluted with toluene (14 ml) and the pH corrected with acetic acid (0.305 g). Toluene (14 ml) and water (1.5 ml) were then added to the mixture and the phases separated after extraction. The collected organic phases were then washed with water (14 ml). The toluene phase was then anhydrified by azeotropic distillation and concentrated until dryness in a rotary evaporator to give a mixture of diastereoisomers of (S)-6-Fluoro-2-(R)-oxiranyl-1-benzopyran and (S)-6-Fluoro-2-(S)-oxiranyl-1-benzopyran 52:48 (0.57 g, 95% yield, 94.4% A).

CHIRALPACK AD-H (250×4.6) mm particles 5 μm, N-Heptane-IPOH (95V-5V), 281 nm, (S)-6-Fluoro-2-(R)-oxiranyl-1-benzopyran: RT=15.36 min; (S)-6-Fluoro-2-(S)-oxiranyl-1-benzopyran: RT=20.32 min.

Diast. SS: $\delta_H$ (400 MHz; CDCl$_3$) 6.81-6.72 (3H, m), 3.88-3.82 (1H, m), 3.21-3.17 (1H, m), 2.89-2.76 (4H, m), 2.1-2.00 (1H, m), 1.97-1.87 (1H, m); Diast. SR: $\delta_H$ (400 MHz; CDCl$_3$) 6.84-6.73 (3H, m), 3.87-3.81 (1H, m), 3.15-3.10 (1H, m), 2.91-2.78 (4H, m), 2.18-2.10 (1H, m), 1.96-1.84 (1H, m).

Example 12

Synthesis of 6-fluoro-2-oxiranyl-1-benzopyran 2.5 g of bromochloromethane (19 mmol) were added at room temperature to a solution of 2.0 g of crude 6-Fluoro-1-benzopyran-2-carboxylic acid methyl ester (9.5 mmol) in 40 ml of THF. The solution was then cooled to −80/−85° C. and 7.8 ml of 2.5 M n-BuLi in hexane (19.5 mmol) were slowly added to maintain the internal temperature between −75° C. and −80° C. The reaction progress was monitored by TLC. A 1 M solution of BH$_3$ in THF (10 ml, 10 mmol) was then slowly added to maintain the internal temperature between −70° C. and −80° C. The reaction progress was monitored by TLC. The mixture was hydrolyzed by the addition of water (15 ml) at 0° C. and the phases separated. A 30% aqueous solution of sodium hydroxide was then added to the organic layer and the mixture warmed up to reflux for 2 h until 2-Chloro-1-(6-fluoro-1-benzopyran-2-yl)-ethanol had disappeared. The biphasic mixture was cooled to 20-25° C., the phases separated. The organic layer was washed with water (5 ml) and concentrated until dryness to give 6-Fluoro-2-oxiranyl-1-benzopyran as a mixture of the 4 diastereoisomers [(R,S);(S,R):(R,R);(S,S)]=52:48 (1.7 g, 91% yield).

The invention claimed is:

1. A process for preparing a compound of formula

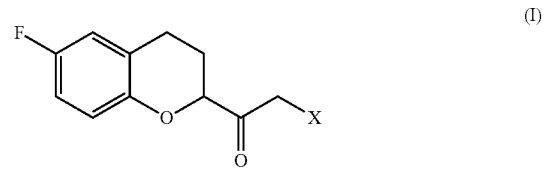

(I)

wherein X is a halogen atom, which comprises reacting a halomethyllithium with a compound of formula

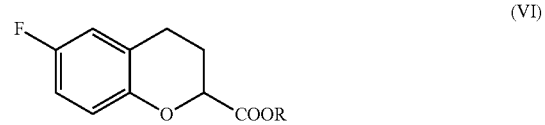

(VI)

wherein R is a (C$_1$-C$_6$)-alkyl group.

2. The process according to claim 1, wherein the halomethyllithium is formed in the reaction system.

3. The process according to claim 2, wherein the halomethyllithium is formed through the addition of an organolithium reagent with a dihalomethane.

4. The process according to claim 3, wherein the dihalomethane is bromochloromethane.

5. The process according to claim 3, wherein the organolithium reagent is n-butyllithium.

6. The process according to claim 3, wherein the compound of formula VI, the dihalomethane and the organolithium reagent are used in a molar ratio of about 1:2:2.

7. The process according to claim 1, wherein the halomethyllithium is chloromethyllithium.

8. The process according to claim 1, wherein the reaction of a compound of formula VI with a halomethyllithium is carried out in the presence of a solvent.

9. The process according to claim 8, wherein the solvent is tetrahydrofuran.

10. The process according to claim 1, wherein the addition of the halomethyllithium to the compound of formula VI is carried out at a temperature in the range from −100° C. to 0° C.

11. The process according to claim 10, wherein the addition of the halomethyllithium is carried out at a temperature in the range from −85° C. to −50° C.

12. A process for preparing a compound of formula

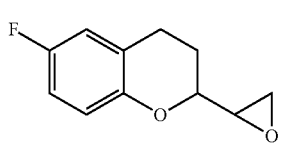
(VII)

which comprises a step of converting a compound of formula VI

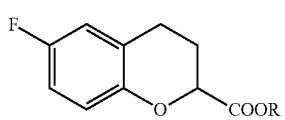
(VI)

wherein R is a $(C_1-C_6)$-alkyl group
into a compound of formula I

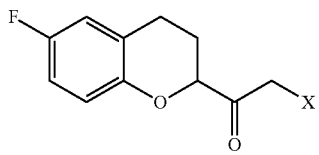
(I)

wherein X is a halogen atom by reacting said compound of formula VI with a halomethyllithium.

13. A process for preparing a compound of formula

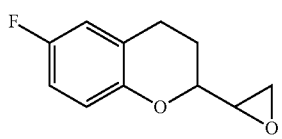
(VII)

which comprises a) reacting with a halomethyllithium a compound of formula

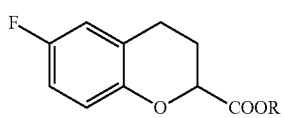
(VI)

wherein R is a $(C_1-C_6)$-alkyl group to give a reaction mixture;
b) in situ reducing said reaction mixture; and
c) cyclizing in the presence of a base.

14. A compound of formula

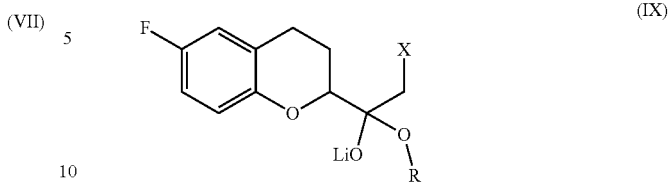
(IX)

wherein X is a halogen atom and R is a $(C_1-C_6)$-alkyl group.

15. The compound according to claim 14, wherein X is chloro and R is methyl.

16. A process for the preparation of nebivolol which comprises a step of converting a compound of formula VI

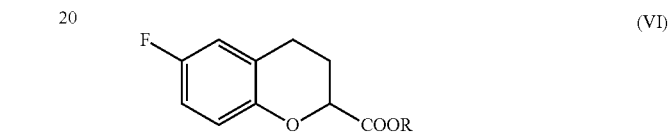
(VI)

wherein R is a $(C_1-C_6)$-alkyl group
into a compound of formula I

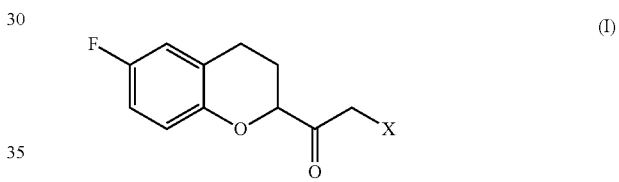
(I)

wherein X is a halogen atom by reacting said compound of formula VI with a halomethyllithium.

17. A process for the preparation of nebivolol which comprises a one-pot conversion of a compound of formula VI

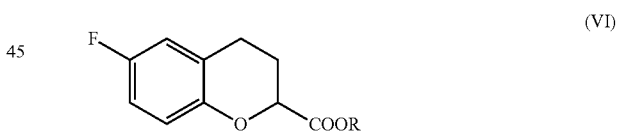
(VI)

wherein R is a $(C_1-C_6)$-alkyl group
into a compound of formula VII

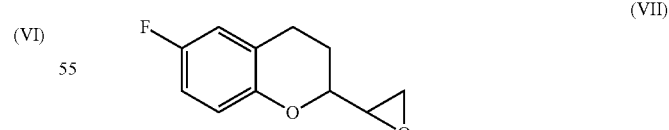
(VII)

said one-pot conversion comprising:
a) reacting said compound of formula VI with a halomethyllithium derivative to give a reaction mixture;
b) in situ reducing said reaction mixture; and
c) cyclizing the resulting product in the presence of a base.

* * * * *